(12) United States Patent
Croxford et al.

(10) Patent No.: US 11,947,722 B2
(45) Date of Patent: Apr. 2, 2024

(54) DEVICES AND HEADSETS

(71) Applicant: Arm Limited, Cambridge (GB)

(72) Inventors: Daren Croxford, Cambridge (GB); Laura Johanna Lähteenmäki, Cambridge (GB)

(73) Assignee: Arm Limited, Cambridge (GB)

(*) Notice: Subject to any disclaimer, the term of this patent is extended or adjusted under 35 U.S.C. 154(b) by 686 days.

(21) Appl. No.: 16/828,506

(22) Filed: Mar. 24, 2020

(65) Prior Publication Data

US 2021/0303070 A1   Sep. 30, 2021

(51) Int. Cl.
| | | |
|---|---|---|
| G06F 3/01 | (2006.01) | |
| A61B 5/00 | (2006.01) | |
| A61B 5/16 | (2006.01) | |
| G02B 27/00 | (2006.01) | |
| G02B 27/01 | (2006.01) | |
| G06F 3/16 | (2006.01) | |
| H04N 13/383 | (2018.01) | |

(Continued)

(52) U.S. Cl.
CPC ............ *G06F 3/015* (2013.01); *A61B 5/163* (2017.08); *A61B 5/4094* (2013.01); *A61B 5/6803* (2013.01); *G02B 27/0093* (2013.01); *G02B 27/0172* (2013.01); *G02B 27/0179* (2013.01); *G06F 3/012* (2013.01); *G06F 3/013* (2013.01); *G06F 3/167* (2013.01); *A61M 2205/507* (2013.01); *G02B 2027/0187* (2013.01); *G06F 3/011* (2013.01); *H04N 13/332* (2018.05); *H04N 13/366* (2018.05); *H04N 13/383* (2018.05); *H04N 13/398* (2018.05)

(58) Field of Classification Search
CPC .......... G06F 3/015; G06F 3/012; G06F 3/013; G06F 3/167; G06F 3/011; A61B 5/163; A61B 5/4094; A61B 5/6803; G02B 27/0093; G02B 27/0172; G02B 27/0179; G02B 2027/0187; A61M 2205/507; H04N 13/332; H04N 13/366; H04N 13/383; H04N 13/398

See application file for complete search history.

(56) References Cited

U.S. PATENT DOCUMENTS 5,311,876 A * 5/1994 Olsen ................... A61B 5/4094
                                                    128/925
7,312,712 B1 * 12/2007 Worrall .................. G08B 21/02
                                                    379/38

(Continued)

FOREIGN PATENT DOCUMENTS

WO     WO2014015378 A1 *  1/2014  ............. G06Q 50/22

*Primary Examiner* — Mihir K Rayan
(74) *Attorney, Agent, or Firm* — EIP US LLP

(57) ABSTRACT

A device has a content processing component operable in a content processing state, and a content transducer configured to provide augmented reality data to a user of the device based on an output of the content processing component. The device has a receiver operable to receive captured data indicative of a health condition of a user of the device. The device has a processor configured to process the captured data to identify a trigger indicative of a possible change in the health condition of a user, and in response to the trigger, modify the content processing state of the content processing component such that at least one characteristic of the augmented reality data is modified.

21 Claims, 10 Drawing Sheets

(51) Int. Cl.
  *H04N 13/332* (2018.01)
  *H04N 13/366* (2018.01)
  *H04N 13/398* (2018.01)

(56) References Cited

U.S. PATENT DOCUMENTS

| | | | | |
|---|---|---|---|---|
| 10,067,565 | B2* | 9/2018 | Ramaprakash | A61B 5/378 |
| 10,169,973 | B2* | 1/2019 | Bostick | G08B 21/0476 |
| 10,210,843 | B2* | 2/2019 | Vinmani | G06F 3/147 |
| 10,595,012 | B2* | 3/2020 | Ross | H04N 13/344 |
| 2002/0035338 | A1* | 3/2002 | Dear | A61B 5/4094 |
| | | | | 600/544 |
| 2007/0276270 | A1* | 11/2007 | Tran | A61B 5/0022 |
| | | | | 600/508 |
| 2010/0264850 | A1* | 10/2010 | Yamamoto | G09G 3/3208 |
| | | | | 315/312 |
| 2014/0268356 | A1* | 9/2014 | Bolas | G02B 27/017 |
| | | | | 359/630 |
| 2014/0316192 | A1* | 10/2014 | de Zambotti | A61B 5/486 |
| | | | | 600/27 |
| 2015/0042679 | A1* | 2/2015 | Jarvenpaa | G06F 3/0304 |
| | | | | 345/633 |
| 2015/0348468 | A1* | 12/2015 | Chen | G09G 3/3413 |
| | | | | 345/207 |
| 2016/0178904 | A1* | 6/2016 | Deleeuw | H04N 13/366 |
| | | | | 345/8 |
| 2017/0169185 | A1* | 6/2017 | Weng | G16H 20/10 |
| 2018/0185665 | A1* | 7/2018 | Osterhout | A61N 5/0618 |
| 2019/0258848 | A1* | 8/2019 | Harrison | G16H 50/20 |
| 2020/0397371 | A1* | 12/2020 | Klosinski, Jr. | A61B 5/7275 |
| 2022/0083986 | A1* | 3/2022 | Duffy | G06Q 10/1097 |

* cited by examiner

DEVICES AND HEADSETS

BACKGROUND OF THE INVENTION

Field of the Invention

The present invention relates to devices and headsets.

Description of the Related Technology

Processing sensor-originated data in relation to augmented reality (AR) environments involves rendering one or more virtual objects in a physical environment to create a composite view for the user in which reality is enhanced by the one or more virtual objects. An alternative term for AR is "mixed reality", which references the merging of real and virtual worlds.

The one or more virtual objects may comprise perceptual information that covers one or more sensory modalities including, for example, visual (in the form of images, which could be text or simple icons in some cases), auditory (in the form of audio), haptic (in the form of touch), somatosensory (relating to the nervous system), and olfactory (relating to the sense of smell) information.

Overlaying the sensory information onto the physical environment can be done constructively (by adding to the natural environment) or destructively (by subtracting from, or masking, the natural environment). AR thus alters a user's perception of their real-world environment.

SUMMARY

According to a first aspect of the present disclosure, there is provided a device comprising: a content processing component operable in a content processing state; a content transducer configured to provide augmented reality data to a user of the device based on an output of the content processing component; a receiver operable to receive captured data indicative of a health condition of a user of the device; and a processor configured to; process the captured data to identify a trigger indicative of a possible change in the health condition of a user; and in response to the trigger, modify the content processing state of the content processing component such that at least one characteristic of the augmented reality data is modified.

According to a second aspect of the present disclosure there is provided a method of operating a device according to the first aspect, the method comprising processing the captured data to identify a trigger indicative of a change in the health condition of a user; and in response to the trigger, modifying the content output of the content processing component such that at least one characteristic of the augmented reality data is modified.

According to a third aspect of the present disclosure there is provided a data carrier comprising machine readable instructions for the operation of one or more processors of a device according to the first aspect of the present disclosure to process the captured data to identify a trigger indicative of a change in the health condition of a user; and in response to the trigger, modify the content output of the content processing component such that at least one characteristic of the augmented reality data is modified.

According to a fourth aspect of the present disclosure, there is provided a device comprising: a content processing component operable in a content processing state; a content transducer configured to provide augmented reality data to a user of the device based on an output of the content processing component; a receiver operable to receive input data indicative of upcoming travel of a user of the device to a different time zone; and a processor configured to; process the input data to identify a destination time zone and a time of travel of a user of the device; and in response to the identification, modify the content processing state of the content processing component such that at least one characteristic of the augmented reality data is modified.

Further features will become apparent from the following description, given by way of example only, which is made with reference to the accompanying drawings.

DETAILED DESCRIPTION OF CERTAIN INVENTIVE EMBODIMENTS

Figure 1:
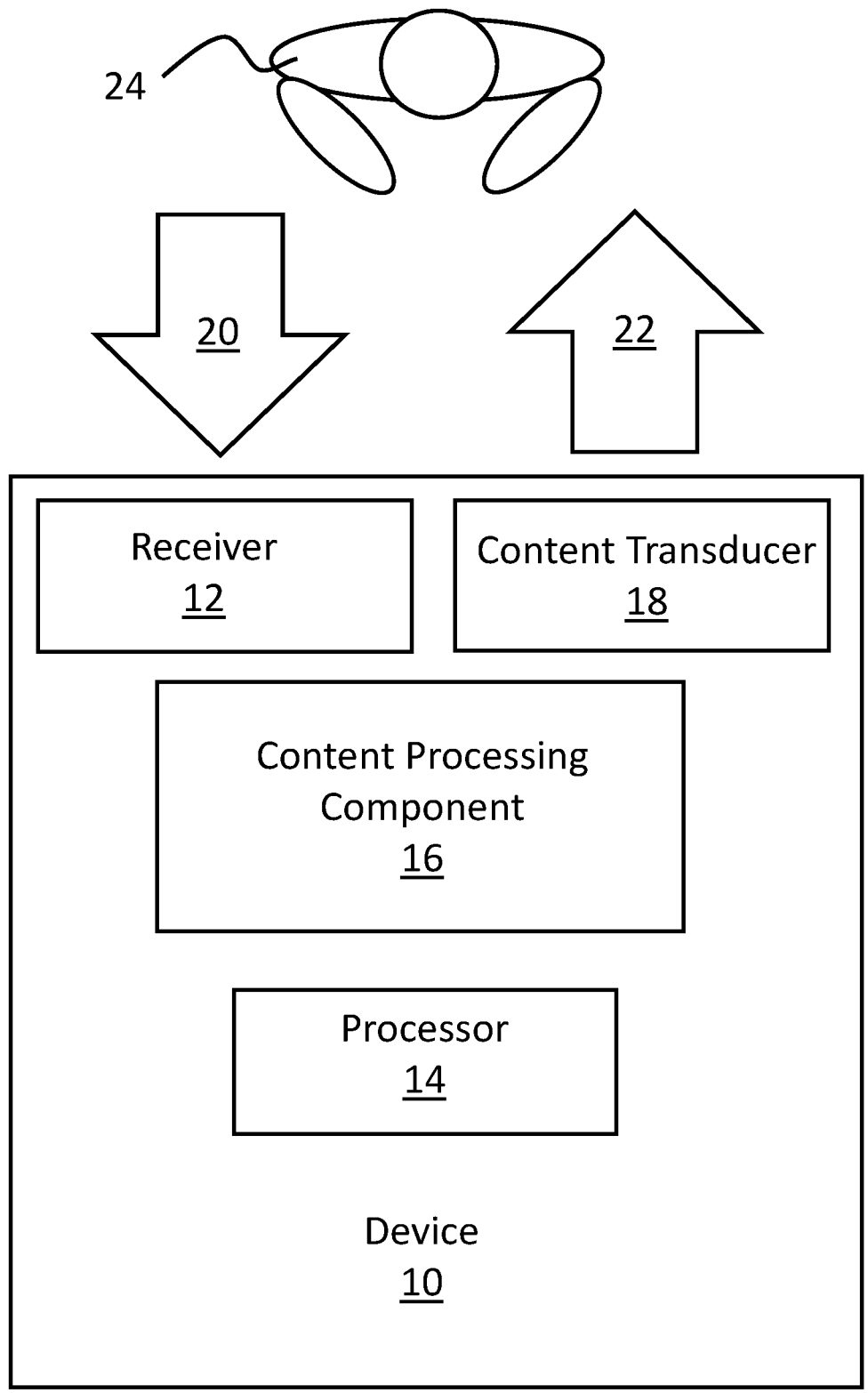
FIG. 1 is a schematic view of a device according to an example.

Details of systems and methods according to examples will become apparent from the following description, with reference to the Figures. In this description, for the purpose of explanation, numerous specific details of certain examples are set forth. Reference in the specification to "an example" or similar language means that a particular feature, structure, or characteristic described in connection with the example is included in at least that one example, but not necessarily in other examples. It should further be noted that certain examples are described schematically with certain features omitted and/or necessarily simplified for ease of explanation and understanding of the concepts underlying the examples.

In some examples herein, devices have a content processing component operable in a content processing state, a content transducer configured to provide augmented reality data to a user of the device based on an output of the content processing component, a receiver operable to receive captured data indicative of a health condition of a user of the device; and a processor configured to, process the captured data to identify a trigger indicative of a possible change in the health condition of a user, and in response to the trigger, modify the content processing state of the content processing component such that at least one characteristic of the augmented reality data is modified.

Thus health conditions of a user of the device may be monitored via interaction of the receiver and the processor, and the device may take steps to modify the augmented reality data provided to the user based on a perceived possible change in the health condition of a user. This may, for example, allow the device to reduce the risk that the augmented reality data to be provided by the device has a negative impact on the user of the device, and may, for example, allow the device to take remedial action where augmented reality data provided by the device is already perceived to have a negative impact on the user.

In some examples herein, devices have a content processing component operable in a content processing state, a content transducer configured to provide augmented reality data to a user of the device based on an output of the content processing component, a receiver operable to receive input data indicative of upcoming travel of a user of the device to a different time zone; and a processor configured to process the input data to identify a destination time zone and a time of travel of a user of the device, and in response to the identification, modify the content processing state of the content processing component such that at least one characteristic of the augmented reality data is modified.

Where humans travel rapidly between time zones, alterations to the body's circadian rhythms may occur, which can cause the physiological condition known as "jet lag". The symptoms of jet lag may be unpleasant, and can include sleep disturbance, dizziness, nausea, confusion, anxiety, increased fatigue, headaches, and digestive issues. In examples of devices herein, a processor is configured to process the input data indicative of upcoming travel of a user of the device to a different time zone to identify a destination time zone and a time of travel of a user of the device, and in response to the identification, modify the content processing state of the content processing component such that at least one characteristic of the augmented reality data is modified. In such a manner, the modified augmented reality data may attempt to account for predicted alterations to the body's circadian rhythms which may cause jet lag, for example with the modified augmented reality data attempting to mitigate for the effects of jet lag by providing augmented reality data representative of a destination time zone of a user of the device.

An example of a device 10 is shown schematically in FIG. 1.

The device 10 may be or may be comprised in a wearable device, for example in the form of a headset. A headset may comprise a head-mounted display (HMD) worn on the head of a user. A HMD typically has one or more display screens, with each display screen corresponding to one or both eyes of the user. The headset may comprise an augmented reality (AR) headset. An AR headset may comprise an opaque display, for example where an image of a surrounding environment is captured by a camera and/or a depth sensor, and virtual objects are generated and combined appropriately with the captured image. An AR headset may comprise a transparent display, for example using waveguide or laser scanning display technology, through which a user can see their surrounding environment, with virtual objects being displayed on the display. The headset may comprise a virtual reality (VR) headset, which generates virtual reality content to be displayed on the display screen(s). A VR or AR headset may comprise an audio content generator and a microphone, for example a transducer in the form of a beeper or speaker or headphones, which generates augmented or virtual noise data, including noise cancellation data, to be provided to a user of the device 10 in use. The headset may comprise an adjustable light source, in form of the display or an external light source.

It will be appreciated that as described herein augmented reality data may be taken to comprise virtual reality data, with both types of data involving the generation of artificial data to be provided to a user of the device 10.

In the example shown schematically in FIG. 1, the device 10 comprises a receiver 12, a processor 14, a content processing component 16, and a content transducer 18. The receiver 12 is communicatively coupled to the processor 14 via a first communication channel, which may use an industry-standard communication technology. The content processing component 16 is communicatively coupled to the processor 14 via a second communication channel, and is communicatively coupled to the content transducer 18 via a third communication channel. Although shown in FIG. 1 as comprising only one each of the receiver 12, the processor 14, the content processing component 16 and the content transducer 18, it will be appreciated that the device 10 may comprise more than one of each of the aforementioned components. The device may also comprise further components not depicted in FIG. 1, including, for example, at least one memory, at least one user interface, and at least one power source.

The receiver 12 is operable to receive captured data 20 indicative of a health condition of a user 24 of the device. The form of the receiver 12 may therefore correspond to a receiver appropriate for the captured data 20 that is desired to be processed by the processor 14. The captured data may be subjected to data processing and signal processing, such as filtering and noise reduction, to quantify the signal of interest. For example, and as discussed in more detail hereafter, the receiver 12 may comprise any or any combination of an eye tracking sensor, an electrical potential sensor, a microphone, a motion tracker, an object recognition system, an accelerometer, a heartbeat monitor, a blood pressure monitor, a camera, a depth sensor, or a software application for receiving schedule information of a user 24 of the device and/or for receiving current date, time and location information. The receiver 12 may receive input data indicative of upcoming travel of the user 24 of the device 10. The captured data 20 may comprise data indicative of an environment of the user 24. For example, the receiver 12 may be operable to receive information about the real-world environment of the user 24. The device 10 may comprise receivers capable of receiving environmental data. In some examples, the captured data may comprise user monitoring data and environmental sensor monitoring data, for example such that the captured data received by the receiver 12 accounts for both the user 24 and the environment of the user 24.

The content processing component 16 is operable in a content processing state, for example a state in which first data is output to the content transducer 18 to prompt the content transducer 18 to provide augmented reality data 22 to a user 24 of the device 10. The content processing component 16 may be operable in plurality of content processing states, with each content processing state generating distinct data that is output to the content transducer 18 to prompt the content transducer 18 to provide augmented reality data 22 to a user 24 of the device 10. In such a manner, augmented reality data 22 provided by the content transducer 18 may be dependent on the content processing state of the content processing component 16. In some examples the content processing component 16 may comprise a graphics processing unit, a video processing unit, an audio processing unit and/or a display processing unit.

The content transducer 18 is configured to provide augmented reality data 22 to a user 24 of the device 10 based on an output of the content processing component 16. The augmented reality data 22 may comprise a virtual object, and the content transducer 18 may be configured to provide a virtual object to a user 24 of the device 10 based on an output of the content processing component 16. A virtual object may comprise perceptual information covering one or more sensory modalities including, for example, visual (in the form of images, which could be text or simple icons in some cases), auditory (in the form of audio), haptic (in the form of touch), somatosensory (relating to the nervous system), and olfactory (relating to the sense of smell) information. The augmented reality data 22 may comprise any or any combination of image content, video content, audio content, and data indicative of external environment conditions perceived by a user 24 of the device 10. The content transducer 18 may comprise any of a display a loudspeaker, headphones, or a vibrating haptic feedback output, for example.

The augmented reality data 22 may be for modifying a representation of a real-world environment for the user 24. For example, the augmented reality data 22 may comprise at least one of audio data or image data. The representation of the real-world environment may similarly comprise at least one of an audio representation or a visual representation. For example, image data may represent a still or moving scene in the real-world environment. Image data may depict a field-of-view of the real-world environment that is capturable by an image sensor, for example. Similarly, audio data may represent instances of sound in the real-world environment that are capturable by an audio sensor. The images and/or audio may be augmented, for example by an AR engine or system, to include one or more virtual objects or features when displayed, for example on the device 10. For example, the virtual objects can be inserted into the images and/or audio to generate an augmented reality environment at the device 10. The one or more virtual objects may be overlaid into the image and/or audio, for example at predetermined locations or anchors, to create the AR environment. As described, one or more other types of perceptual information may be used for the representation of the real-world environment and the virtual objects, for example haptic data, somatosensory data or olfactory data.

In examples, a virtual object may be an AR object retrievable from an object library of stored virtual objects, as part of an AR platform implemented on the device 10. At least part of the object library may be stored in memory on the user device, with further portions of the object library being stored remotely via the cloud, for example. The virtual object may be represented in the form of corresponding virtual object data. Thus, the virtual object may be inserted into the representation of the real-world environment, comprising at least one of image or audio data, based on the virtual object data corresponding to the virtual object. Auxiliary data may be used to assist insertion of the virtual object into the representation of the real-world environment. For example, where a virtual image object is inserted into a visual representation of the real-world environment, spatial data, and potentially depth data, may be applied to the virtual object data, or vice versa, in order to insert the virtual object at a determined position, orientation and/or scale in the image.

The processor 14 is configured to process the captured data 20 received by the receiver 12 to identify a trigger indicative of a possible change in the health condition of the user 24. The trigger will, of course, depend on the captured data 20 received by the receiver 12, and examples of triggers will be discussed in more detail hereafter. In response to the trigger, the processor 14 is configured to modify the content processing state of the content processing component 16 such that at least one characteristic of the augmented reality data 22 is modified. The modification will depend on the captured data 20 and the possible change in the health condition of the user 24, with appropriate modifications being discussed in further detail hereafter. Thus health conditions of a user 24 of the device 10 may be monitored via interaction of the receiver 12 and the processor 14, and the device 10 may take steps to modify the augmented reality data 22 provided to the user 24 based on a perceived possible change in the health condition of the user 24. This may, for example, allow the device 10 to reduce the risk that the augmented reality data 22 to be provided by the device 10 has a negative impact on the user 24 of the device 10, and may, for example, allow the device 10 to take remedial action where augmented reality data 22 provided by the device 10 is already perceived to have a negative impact on the user 24. This can, for example, be used to reduce the negative impact of environment, such as noise or excessive visual triggers.

Figure 2:
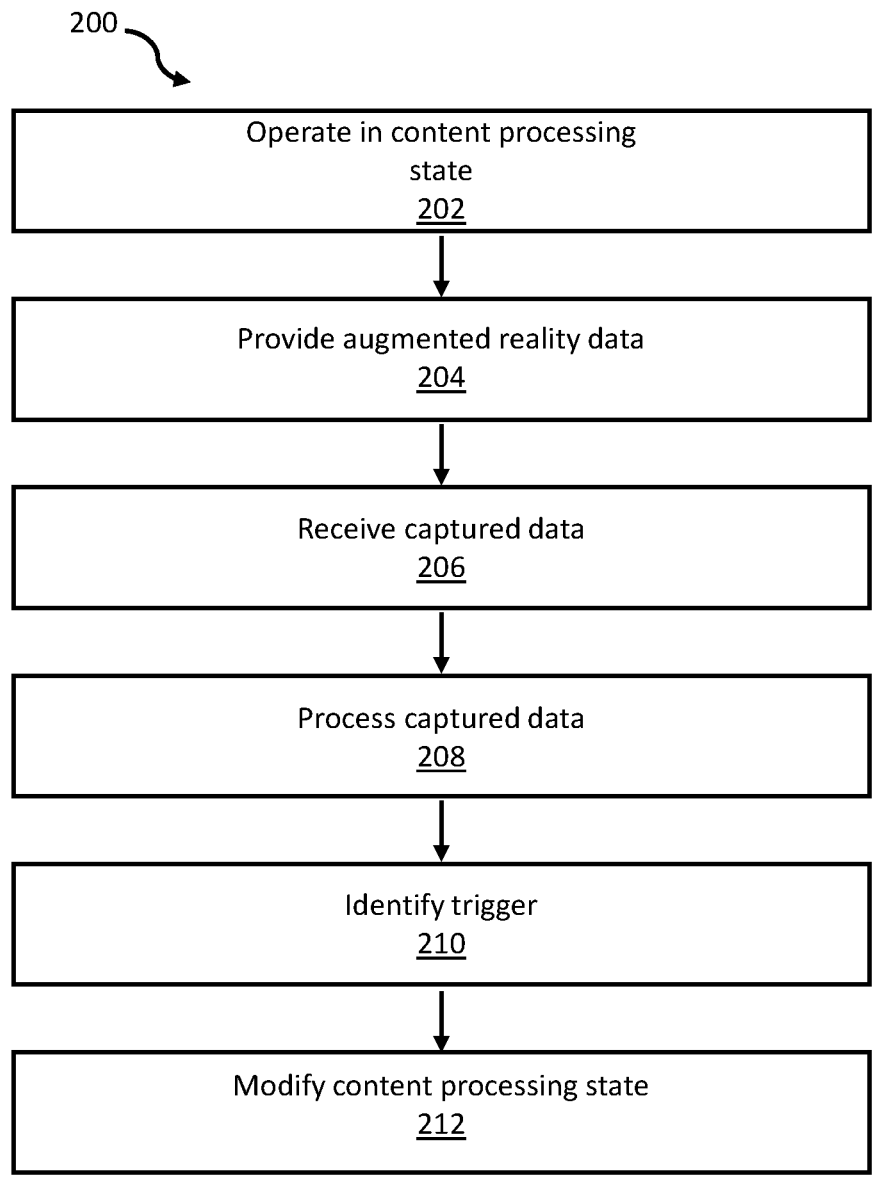
FIG. 2 is a schematic view illustrating a first method of operating a device according to an example.

Examples of the steps taken in controlling the device 10 are shown schematically by a method 200 in FIG. 2.

The method 200 comprises operating 202 the content processing component 16 in a content processing state, and providing 204, via the content transducer 18, augmented reality data 22 to a user 24 of the device 10 based on an output of the content processing component 16. The method comprises receiving 206, via the receiver 12, captured data 20 indicative of a health condition of the user 24 of the device 10. The captured data 20 is processed 208 by the processor 14 to identify 210 a trigger indicative of a possible change in the health condition of the user 24, and in response to identification of the trigger, the content processing state of the content processing component 16 is modified 212 such that at least one characteristic of the augmented reality data 22 is modified.

In an example of the device 10, the receiver 12 may comprise an eye tracking sensor for monitoring a location of an eye of the user 24 of the device 10. An eye tracking sensor may comprise an optical eye tracking sensor which is able to track the motion of one or more eyes of a user by detecting light reflected from the eye of the user with a video camera or other sensor. Eye tracking sensors may indicate current eye positional characteristics, and may provide accurate eye location information. Additionally, the data output by the eye tracking sensor may be used to identify or recognize a visual object that the user is looking at.

Alternatively or additionally, an eye tracking sensor may comprise an electrical potential eye tracking sensor which utilizes electrical potentials measured within one or more electrodes placed around the eye of a user. For example, the eye tracking sensor may utilize electroencephalography (EEG), electromyography (EMG), or electrooculography (EOG) signal detection to track motion of the eye of a user. Electrical potential eye tracking sensors may provide an indication of movement before movement actually begins, and hence may provide low latency.

In such an example of the device 10, the content transducer 18 may comprise a visual display, and the augmented reality data 22 may comprise a virtual object displayed on the display.

Where the receiver 12 comprises an eye tracking sensor for monitoring a location of an eye of the user 24 of the device 10, the trigger may comprise eye movements of the user 24 of the device. For example, the trigger may comprise a determination that eye movements of the user 24 are rapid, or involuntary. Rapid or involuntary eye movements may, for example, be indicative of any of attention deficit hyperactivity disorder (ADHD), epilepsy, or autism, amongst other health conditions. The trigger may comprise a speed threshold for speed of motion of an eye of the user. The eye tracking sensor may detect positional and time-based data relating to the eye of the user, and the processor 14 may be configured to process the positional and time-based data to determine a speed of motion of the eye. The eye tracking sensor may be capable of detecting blinking of an eye of the user 24, for example by detecting the presence or absence of reflected light from the eye of the user 24, and the trigger may comprise a determination that a blink rate is above a pre-determined threshold. A high blink rate may be indicative of ADHD behavior, for example.

Modification of the content processing state of the content processing component 16 such that at least one characteristic of the augmented reality data 22 is modified may allow the device 10 to reduce the risk that the augmented reality data 22 to be provided by the device 10 has a negative impact on the user 24 of the device 10 by triggering one of the health conditions indicated above, and may, for example, allow the device 10 to take remedial action where augmented reality data 22 provided by the device 10 is already perceived to have a negative impact on the user 24 by having triggered one of the health conditions mentioned above.

In an example, the trigger may comprise fixation of an eye of a user on at least one attribute of the augmented reality data 22, and the receiver 12 may, for example, comprise an eye tracking sensor for monitoring a location of an eye of the user 24 of the device 10. Fixation of an eye of the user 24 on an attribute of the augmented reality data 22 may be indicative of a possible change in health condition of the user 24. Fixation of an eye of a user may be determined where an eye of a user is fixed at a particular location for a time period exceeding a pre-determined threshold. For example, a user 24 suffering with depression may be more likely to focus on augmented reality data 22, including data indicative of the external environment, which is indicative of a negative emotional response (eg unhappy subjects displayed as part of the augmented reality data 22), and so where fixation on augmented reality data 22 which is indicative of a negative emotional response is detected, the content processing state of the content processing component 16 may be modified such that at least one characteristic of the augmented reality data 22 is modified to relieve depression of the user 24.

In some examples, the trigger may comprise fixation of an eye of the user on a particular subject provided as part of the augmented reality data 22, for example a particular object displayed as part of the augmented reality data 22. Fixation on a particular subject may be taken to be indicative of excessive stimuli provided by the subject, which may, in some cases, be indicative of ADHD and/or autism, for example.

In some examples, the trigger may comprise fixation of an eye of the user 24 on a particular region of a display forming part of the content transducer 18. Fixation to the right of the user 24 or fixation downwardly toward the ground may be indicative of depression, and so where fixation to the right of the user 24 or fixation downwardly toward the ground is detected, the content processing state of the content processing component 16 may be modified such that at least one characteristic of the augmented reality data 22 is modified to relieve depression, for example seasonal affective disorder (SAD), of the user 24. The device 10 may also provide an indication to the user 24 that they are experiencing depression.

Figure 3:
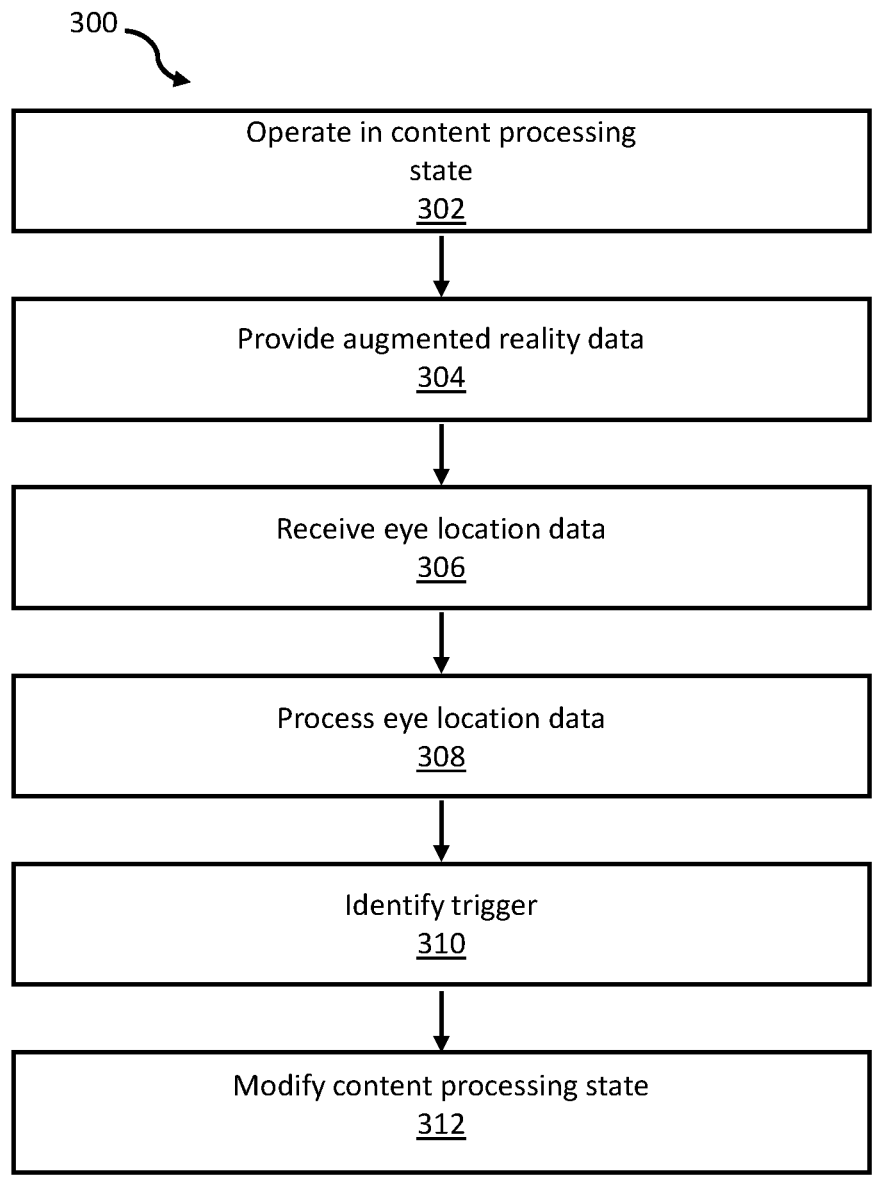
FIG. 3 is a schematic view illustrating a second method of operating a device according to an example.

A method 300 of operating a device 10 where the receiver 12 comprises an eye tracking sensor for monitoring a location of an eye of the user 24 of the device 10 is shown schematically in FIG. 3. The method 300 comprises operating 302 the content processing component 16 in a content processing state, and providing 304, via the content transducer 18, augmented reality data 22 to a user 24 of the device 10 based on an output of the content processing component 16. The method comprises receiving 306, via a receiver 12 in the form of an eye tracking sensor, data indicative of a location of an eye of the user 24 of the device 10. The data indicative of a location of an eye of the user 24 is processed 308 by the processor 14 to identify 310 a trigger indicative of a possible change in the health condition of the user 24, and in response to identification of the trigger, the content processing state of the content processing component 16 is modified 312 such that at least one characteristic of the augmented reality data 22 is modified.

In an example, the receiver 12 may comprise an eye tracking sensor for monitoring a size of a pupil of the user 24 of the device 10, and the trigger may comprise dilation of a pupil of the user 24. For example, dilation of a pupil may be indicative of ADHD behavior, and so the content processing state of the content processing component 16 may be modified such that at least one characteristic of the augmented reality data 22 is modified where a trigger indicative of ADHD behavior is detected. Dilation of a pupil of a user 24 may occur, for example, where a user focusses on a subject provided as part of the augmented reality data 22. Dilation of an eye of a user may be determined where, for example, the size of a pupil of a user increases by more than a pre-determined threshold.

Figure 4:
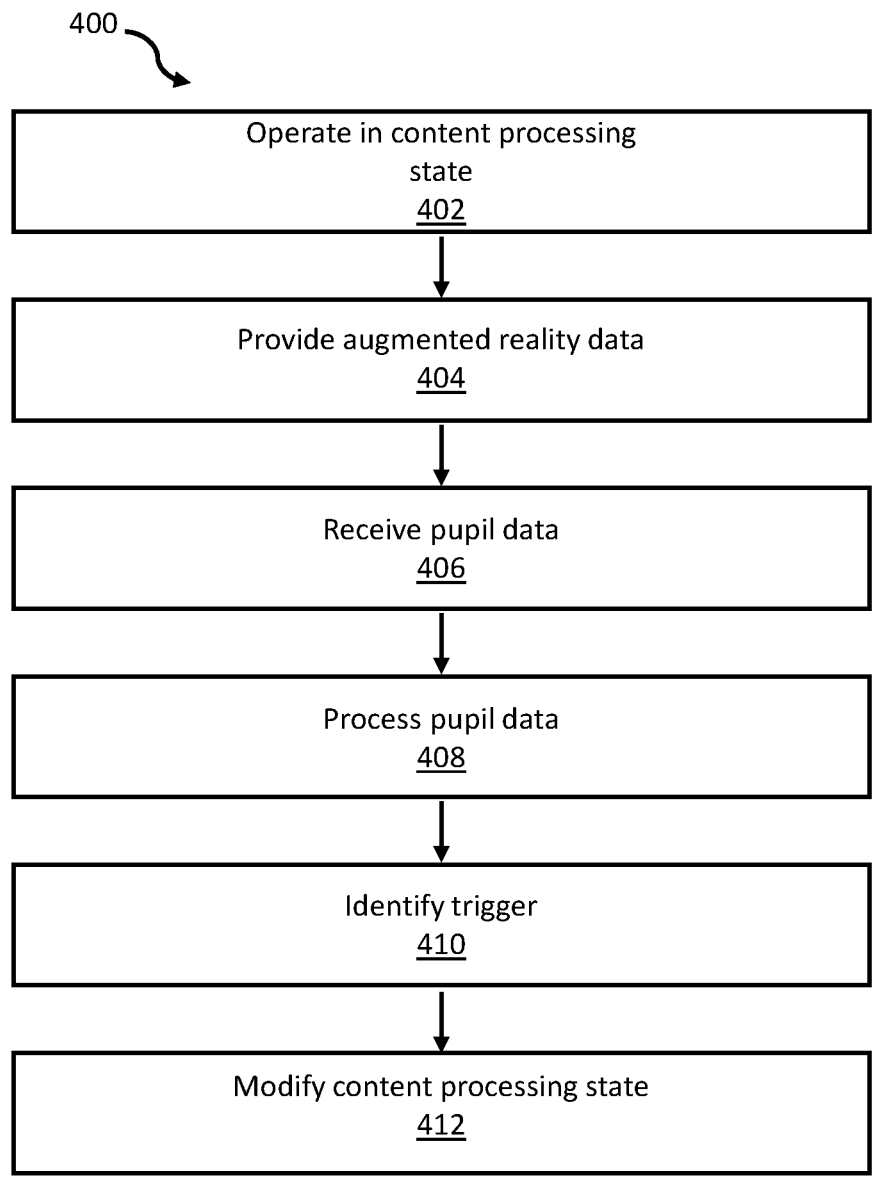
FIG. 4 is a schematic view illustrating a third method of operating a device according to an example.

A method 400 of operating a device 10 where the receiver 12 comprises an eye tracking sensor for monitoring a size of a pupil of the user 24 of the device 10 is shown schematically in FIG. 4. The method 400 comprises operating 402 the content processing component 16 in a content processing state, and providing 404, via the content transducer 18, augmented reality data 22 to a user 24 of the device 10 based on an output of the content processing component 16. The method comprises receiving 406, via a receiver 12 in the form of an eye tracking sensor, data indicative of a size of a pupil of an eye of the user 24 of the device 10. The data indicative of a size of a pupil of an eye of the user 24 is processed 408 by the processor 14 to identify 410 dilation of the pupil, and in response to identification of dilation of the pupil, the content processing state of the content processing component 16 is modified 412 such that at least one characteristic of the augmented reality data 22 is modified.

In some examples, the receiver 12 may comprise an electrical potential sensor for monitoring electrical potential signals of the user 24 of the device 10, and the trigger may comprise a pattern in monitored electrical potential signals. For example, the receiver 12 may comprise an electroencephalogram (EEG) sensor for monitoring electrical potential signals of the user 24 of the device 10. Electrical potential signals of the user 24 of the device 10 may be indicative of potential changes in health conditions of the user 24. For example, EEG signals may be indicative of ADHD behavior, an epileptic seizure, or depression, and/or EEG signals may be used to determine motion of an eye of the user 24 of the device 10.

Figure 5:
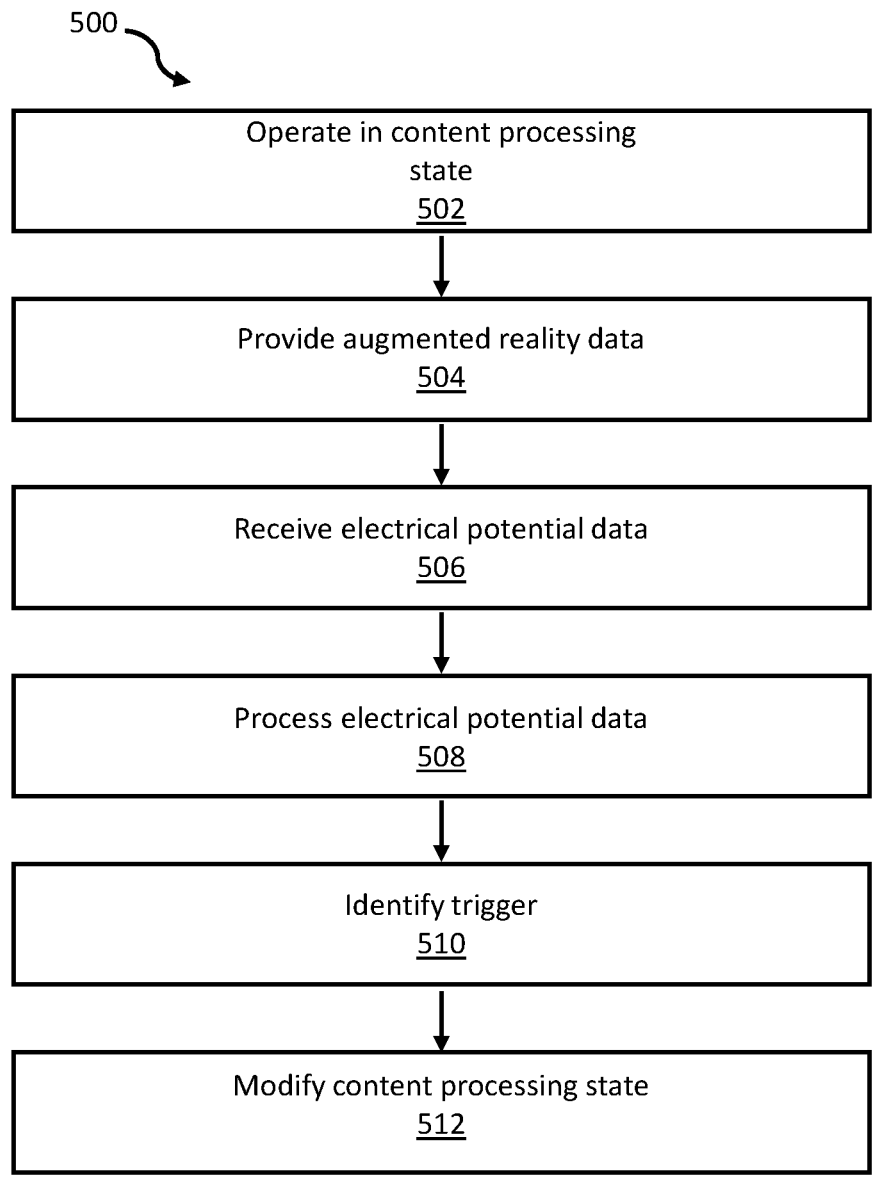
FIG. 5 is a schematic view illustrating a fourth method of operating a device according to an example.

A method 500 of operating a device 10 where the receiver 12 comprises an electrical potential sensor for monitoring electrical potential signals of the user 24 of the device 10 is shown schematically in FIG. 5. The method 500 comprises operating 502 the content processing component 16 in a content processing state, and providing 504, via the content transducer 18, augmented reality data 22 to a user 24 of the device 10 based on an output of the content processing component 16. The method comprises receiving 506, via a receiver 12 in the form of an electrical potential sensor, data indicative of electrical potential signals of the user 24 of the device 10. The data indicative of electrical potential signals of the user 24 is processed 508 by the processor 14 to identify 510 a trigger indicating a possible change in a health condition of the user 24, and in response to the trigger, the content processing state of the content processing component 16 is modified 512 such that at least one characteristic of the augmented reality data 22 is modified.

In an example, the receiver 12 may comprise a microphone, and the trigger may comprise an increase in noise levels and/or number of audio sources received by the microphone in use. Users suffering from autism can suffer from information overload in their surrounding environment, and hence increases in noise levels and/or the number of audio sources present may have a potential negative impact on a user suffering from autism. The trigger may comprise a determination that a noise level has exceeded a pre-determined noise threshold. The trigger may comprise a determination that a number of audio sources has increased beyond a pre-determined threshold.

Figure 6:
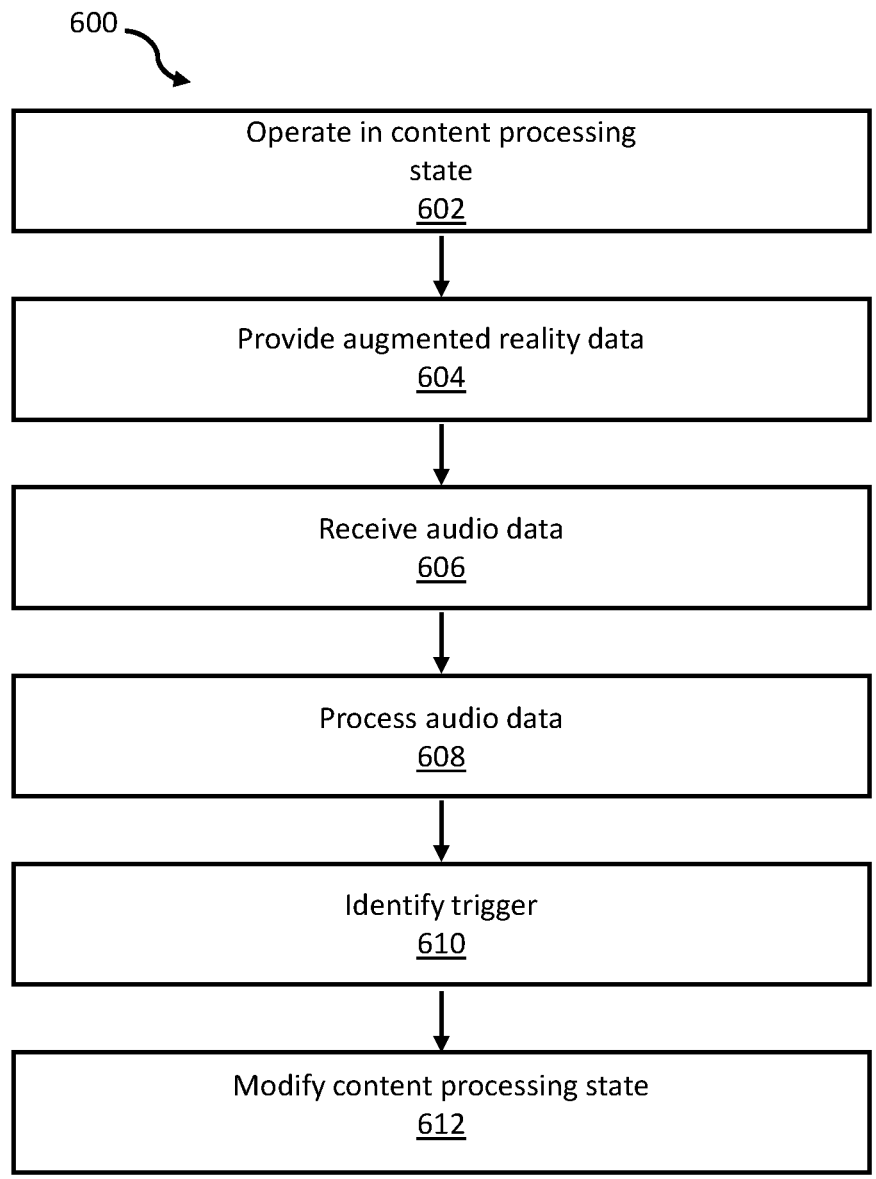
FIG. 6 is a schematic view illustrating a fifth method of operating a device according to an example.

A method 600 of operating a device 10 where the receiver 12 comprises a microphone is shown schematically in FIG. 6. The method 600 comprises operating 602 the content processing component 16 in a content processing state, and providing 604, via the content transducer 18, augmented reality data 22 to a user 24 of the device 10 based on an output of the content processing component 16. Here the augmented reality data 22 comprises at least one audio object. The method comprises receiving 606, via a receiver 12 in the form of a microphone, data indicative of audio levels and/or audio sources of a surrounding environment of the user 24 of the device 10. The data indicative of audio levels and/or audio sources is processed 608 by the processor 14 to identify 610 an increase in noise levels and/or number of audio sources, and in response to an increase the content processing state of the content processing component 16 is modified 612 such that at least one characteristic of the augmented reality data 22 is modified.

In such an example of the device 10, the content transducer 18 may comprise a loudspeaker, and the augmented reality data 22 may comprise a virtual object output by the loudspeaker.

In some examples, the receiver 12 may comprise an object recognition system for recognising objects of an external environment of a user of the device, and the trigger may comprise an object of an external environment of a user of the device. Objects of an external environment of a user of the device may have the potential to negatively impact a health condition of the user 24 of the device 10. For example, certain types or classes of objects may cause or enhance any of ADHD behavior, epileptic seizures, excessive stimuli for autism, and depression. By recognising such objects using an object recognition system, the processor 14 is able to modify the content processing state of the content processing component 16 such that at least one characteristic of the augmented reality data 22 is modified to mitigate for any potential negative effects caused by the objects.

A photosensitive light source may be considered to be a potential cause of an epileptic seizure, and hence the trigger may comprise a determination that a photosensitive light source is present in the augmented reality data 22. It may also comprise a determination that the amount of light is excessive or that the light is distracting e.g. due to flashing. The modification of the content processing state may then cause a modification of the augmented reality data 22 such that the representation of the photosensitive light source is modified, for example obscured within or removed from the augmented reality data 22. In some examples, certain objects and/or numbers of objects may be considered to be potential causes of sensory overload, and the trigger may comprise a determination that certain pre-determined object and/or a number of pre-determined objects are present in the augmented reality data 22. The modification of the content processing state may then cause a modification of the augmented reality data 22 such that the pre-determined object is obscured or removed from the augmented reality data 22, or a modification such that the number of objects provided as part of the augmented reality data 22 is decreased.

The object recognition system (or "object detection system", "object identification system", "object classifier") may be configured to detect instances of objects of a certain class in the real-world environment, e.g. image/audio representations thereof. For example, the object recognition system may obtain sensor-originated data, e.g. image and/or audio data, as input and determine whether one or more objects of a predetermined class are present in the sensor-originated data or the real-world environment represented thereby. For example, where the predetermined class is human faces, the object recognition system may be used to detect the presence of a human face in the sensor-originated data or the real-world environment.

In some cases, an object recognition system allows particular instances of the object to be identified. For example, the instance may be a particular human face. Other examples of such object recognition include recognizing, or detecting, instances of expressions (e.g. facial expressions), gestures (e.g. hand gestures), audio (e.g. recognizing one or more particular sounds in an audio environment), heat signatures (e.g. recognizing objects such as faces in an infrared representation or "heatmap"). Thus, in examples, the type of "object" being detected may correspond with the type of representation of the real-world environment. For example, for a visual or image representation, which may include depth information, of the real-world environment, the object recognition may involve recognizing particular articles, expressions, gestures, etc. whereas for an audio representation of the real-world environment the object recognition may involve recognizing particular sounds or sources of sound. In some examples, the object recognition may involve detecting a motion of a recognized object. For example, as well as recognizing an instance of a particular type of object, e.g. a car, in the audio/visual representation of the real-world environment, the object recognition system may also detect or determine a motion of the instance of the object, e.g. the recognized car. Thus, the object recognition data may include object motion data, e.g. representative of a detected or determined motion of the object in the real-world environment.

In examples, the object recognition system may comprise, or implement, a support vector machine (SVM), segmented simultaneous location and mapping (SLAM), classic computer vision algorithms, or neural network to perform the object recognition, though many other types of object recognition system exist. The object recognition data may thus correspond to the output of an object recognition process performed by the object recognition system.

A neural network typically includes several interconnected neurons forming a directed, weighted graph in which vertices (corresponding to neurons) or edges (corresponding to connections) of the graph are associated with weights, respectively. The weights may be adjusted throughout training of the neural network for a particular purpose, altering the output of individual neurons and hence of the neural network as a whole. In a convolutional neural network (CNN), convolutional layers are used to convolve an input and pass the result to the next layer. A fully connected layer typically connects every neuron in one layer to every neuron in another layer. Fully connected layers may therefore be used to identify overall characteristics of an input, such as whether an object of a particular class, or a particular instance belonging to the particular class, is present in an input (e.g. image, video, sound) as part of an object classification process.

Figure 7:
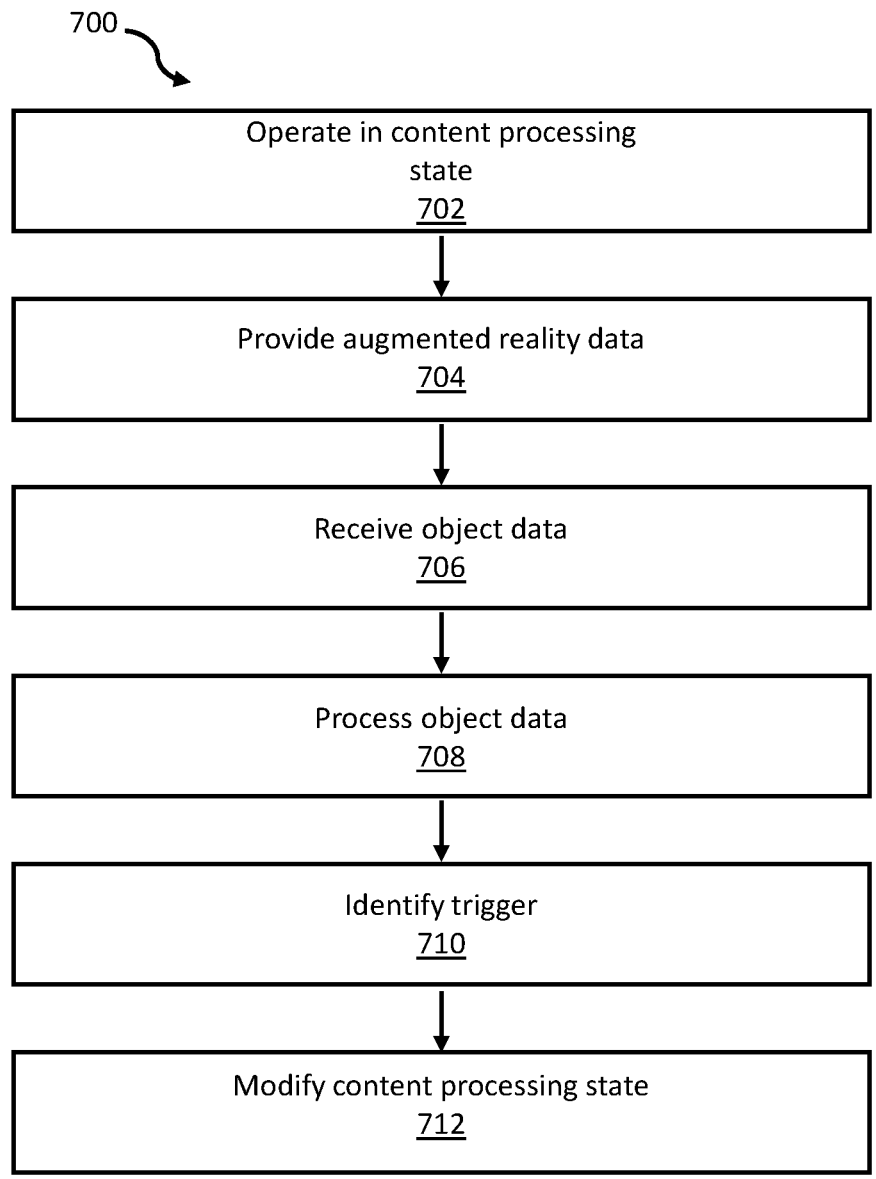
FIG. 7 is a schematic view illustrating a sixth method of operating a device according to an example.

A method 700 of operating a device 10 where the receiver 12 comprises an object recognition system is shown schematically in FIG. 7. The method 700 comprises operating 702 the content processing component 16 in a content processing state, and providing 704, via the content transducer 18, augmented reality data 22 to a user 24 of the device 10 based on an output of the content processing component 16. The method comprises receiving 706, via a receiver 12 in the form of an object recognition system, data indicative of objects of an external environment of the user 24 of the device 10. The data indicative of objects of the external environment is processed 708 by the processor 14 to identify 710 a trigger indicative of possible change to a health condition of the user 24, and in response to the trigger the content processing state of the content processing component 16 is modified 712 such that at least one characteristic of the augmented reality data 22 is modified.

In some examples, the receiver may comprise a software application for receiving schedule information of the user 24 of the device 10, and the trigger may comprise a determination from the schedule information that the user intends to travel to another time zone. The software application may, for example, comprise an application stored in memory of the device 10 and capable of being run on the device 10. The software application may comprise a calendar application which indicates the user's schedule, or may comprise a messaging application, for example an e-mail application, which reads a user's message to extract schedule information. In some examples, a user may manually input schedule information into the software application. In some examples, the software information may automatically extract schedule information, and may, for example, display a prompt to the user to confirm modification in response to the trigger. The software application may receive schedule information from a remote device belonging to the user 24, for example from a mobile telephone or other computing device of the user 24.

Where humans travel rapidly between time zones, alterations to the body's circadian rhythms may occur which can cause the physiological condition known as "jet lag". The symptoms of jet lag may be unpleasant, and can include sleep disturbance, dizziness, nausea, confusion, anxiety, increased fatigue, headaches, and digestive issues. As the device 10 may recognise that the user intends to travel to another time zone, and the content processing state of the content processing component is modified such that at least one characteristic of the augmented reality data is modified, the modification of the augmented reality data may be used to mitigate for any potential jetlag effects that may be caused by the user's upcoming travel. For example, light displayed to the user may be modified in response to the trigger. In particular, this may include exposure to light at certain times to ease the transition to a new time zone. It may also include reducing the exposure to light in order to simulate nighttime conditions.

Figure 8:
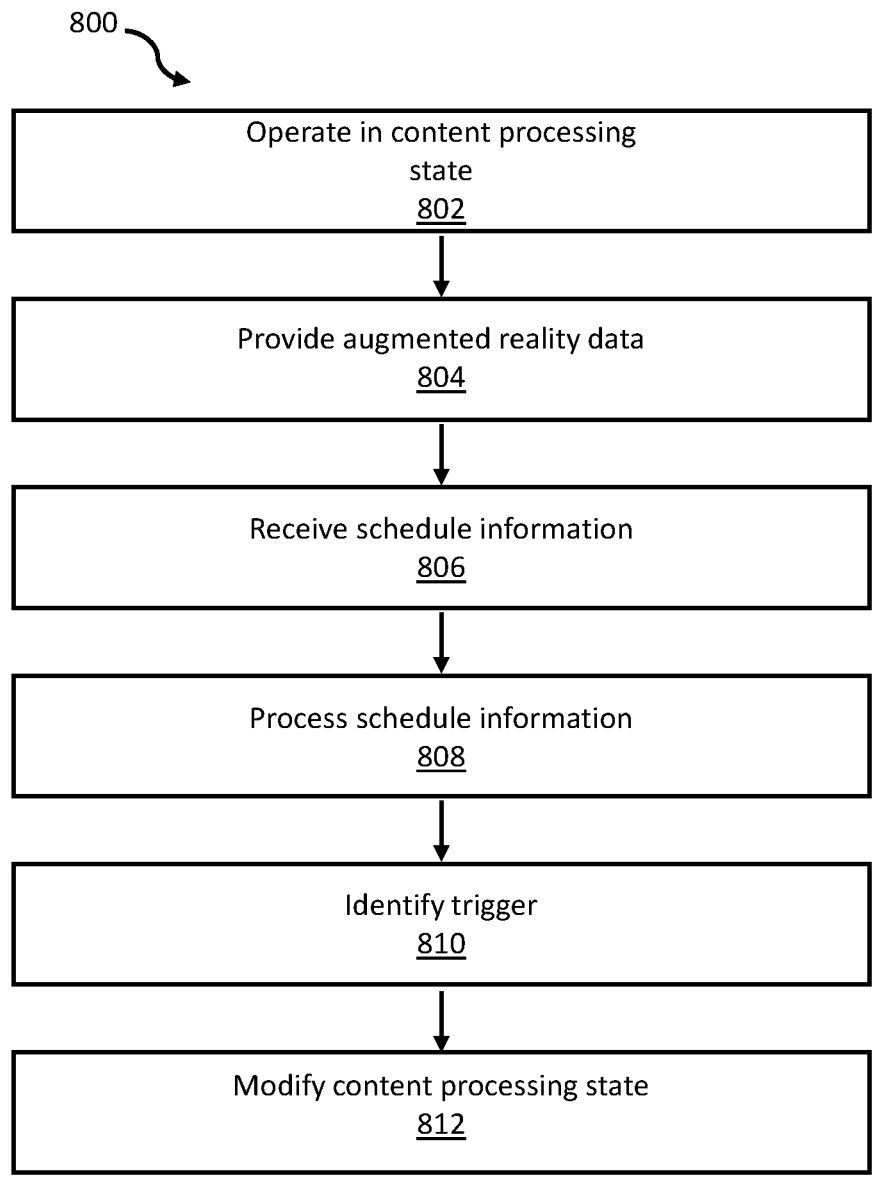
FIG. 8 is a schematic view illustrating a seventh method of operating a device according to an example.

A method 800 of operating a device 10 where the receiver 12 comprises a software application for receiving schedule information of the user 24 of the device 10 is shown schematically in FIG. 8. The method 800 comprises operating 802 the content processing component 16 in a content processing state, and providing 804, via the content transducer 18, augmented reality data 22 to a user 24 of the device 10 based on an output of the content processing component 16. The method comprises receiving 806, via a receiver 12 in the form of a software application for receiving schedule information of the user 24 of the device 10, data indicative of upcoming travel of the user 24 of the device 10. The data indicative of upcoming travel is processed 808 by the processor 14 to identify 810 travel to a different time zone, and in response to identified travel to a different time zone the content processing state of the content processing component 16 is modified 812 such that at least one characteristic of the augmented reality data 22 is modified.

In some examples, the receiver 12 may comprise a software application for receiving current date, time and location information, and the trigger may comprise a determination that the current date, time and location information or the environmental conditions related thereto have a potential negative impact on a mental or physical state of a user of the device. For example, seasonal affective disorder (SAD) may cause depression at certain times of the year, and such depression may be detected as previously described herein. By utilizing current date, time and location information, for example in combination with other factors to determine depression, it may be determined that the user 24 of the device 10 is suffering from SAD, and at least one characteristic of the augmented reality data 22 may be modified accordingly. For example, the augmented reality data 22 can be made brighter by adjusting a light source of the device 10. In some examples, the receiver 12 may also receive an indication of a light level for a given detected location.

Figure 9:
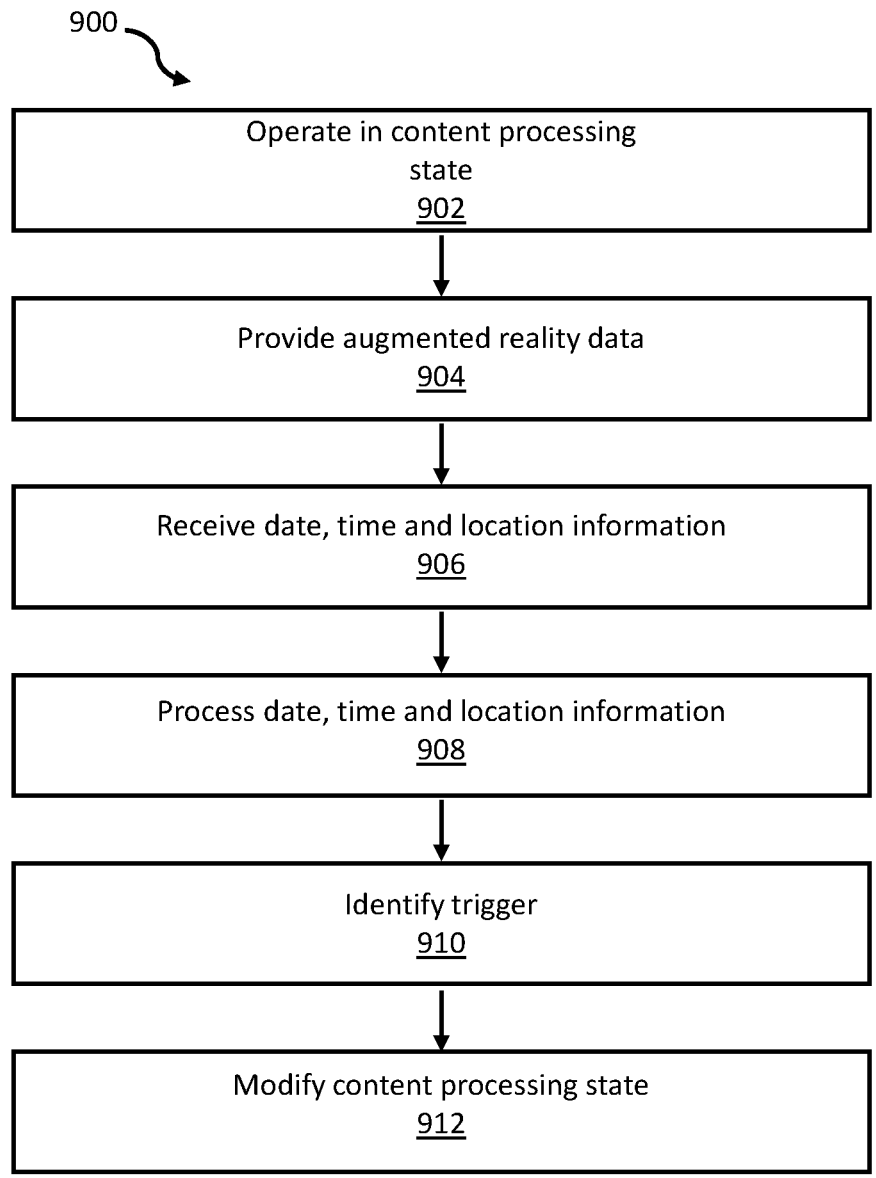
FIG. 9 is a schematic view illustrating an eighth method of operating a device according to an example.

A method 900 of operating a device 10 where the receiver 12 comprises a software application for receiving current date, time and location information is shown schematically in FIG. 9. The method 900 comprises operating 902 the content processing component 16 in a content processing state, and providing 904, via the content transducer 18, augmented reality data 22 to a user 24 of the device 10 based on an output of the content processing component 16. The method comprises receiving 906, via a receiver 12 in the form of a software application, current date, time and location information. The current date, time and location information is processed 908 by the processor 14 to identify 910 a possible change to a health condition of the user 24, and in response to identification of a possible change the content processing state of the content processing component 16 is modified 912 such that at least one characteristic of the augmented reality data 22 is modified.

In some examples, the receiver 12 may comprise a motion tracker for tracking motion of a head of the user 24 of the device 10, and the trigger may comprise a determination of a position of a head of the user 24 of the device 10. For example, the motion tracker may be configured to monitor a head position and/or a speed of change of head position of the user 24 of the device 10. Motion of a head of the user 24 of the device 10 can, in certain circumstances, be indicative of depression. For example, slower head movement and/or less changes in head position may be indicative of depression of the user 24 of the device 10. The trigger may comprise a determination that the head of the user 24 is moving at a speed below a pre-determined threshold, and/or a determination that the head of the user 24 is located at a number of positions below a pre-determined threshold number of positions during a given time period. The motion tracker may comprise an accelerometer and/or a gyroscope.

Figure 10:
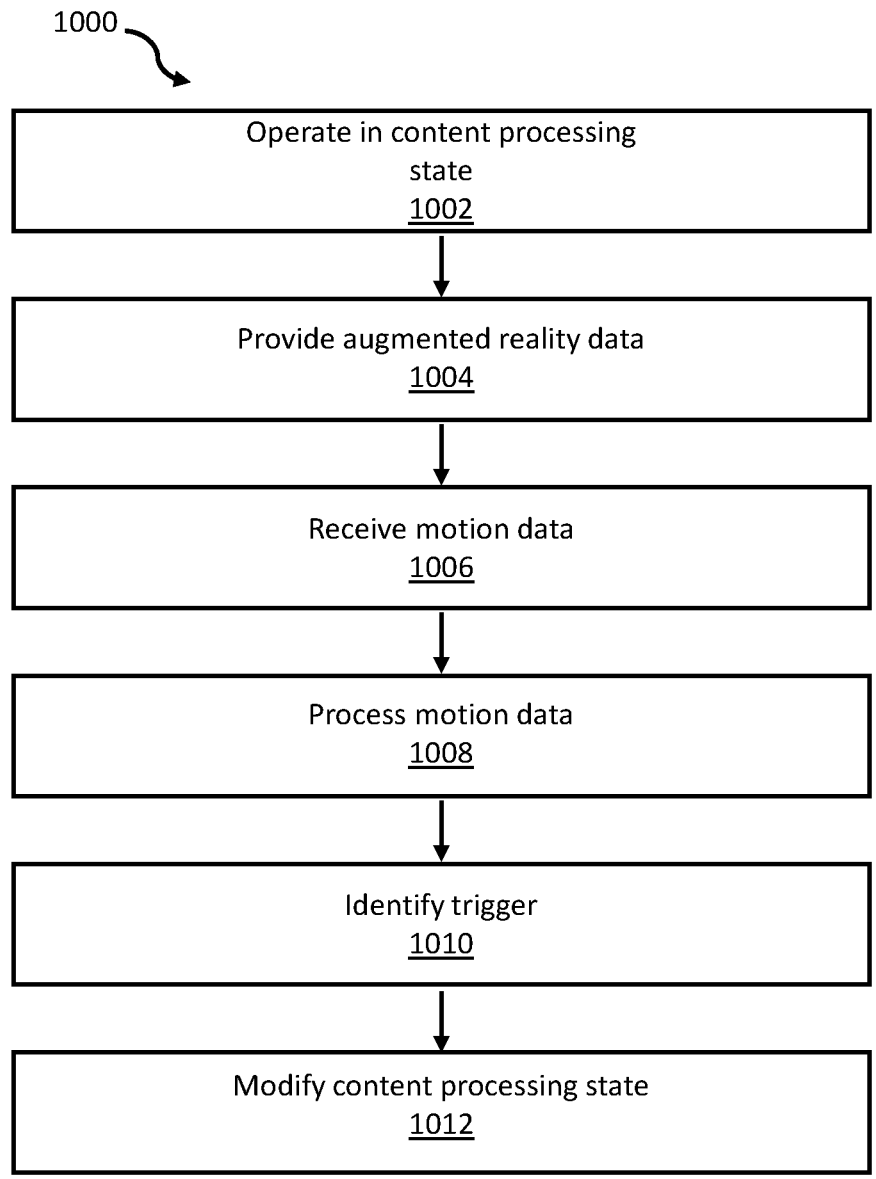
FIG. 10 is a schematic view illustrating a ninth method of operating a device according to an example.

A method 1000 of operating a device 10 where the receiver 12 comprises a motion tracker for tracking motion of a head of the user 24 of the device 10 is shown schematically in FIG. 10. The method 1000 comprises operating 1002 the content processing component 16 in a content processing state, and providing 1004, via the content transducer 18, augmented reality data 22 to a user 24 of the device 10 based on an output of the content processing component 16. The method comprises receiving 1006, via a receiver 12 in the form of a motion tracker, data indicative of motion of a head of the user 24 of the device 10. The data indicative of motion of a head of the user 24 is processed 1008 by the processor 14 to identify 1010 a possible change to a health condition, or a pre-existing health condition of the user 24, and in response to identification of a possible change the content processing state of the content processing component 16 is modified 1012 such that at least one characteristic of the augmented reality data 22 is modified.

In some examples, the receiver 12 is operable to receive data indicative of any of attention deficit hyperactivity disorder, epilepsy, autism, depression, seasonal affective disorder, or jetlag.

As discussed for the examples above, at least one characteristic of the augmented reality data 22 is modified in response to a trigger. It will of course be appreciated that the at least one characteristic of the augmented reality data 22 that is modified may depend on the augmented reality data 22 provided, as well as the determined possible change in the health condition of the user 24.

In some examples, the augmented reality data 22 comprises video content, and the at least one characteristic of the augmented reality data 22 is any of video content brightness, video content speed, video content quality, number of objects provided as video content, presence of video content, or refresh rate of video content. Increasing video brightness may, for example, mitigate for the effects of SAD by displaying brighter imagery to the user 24. Reduced number of objects provided as video content may reduce the sensory burden on a user 24. Reducing refresh rate of video content may reduce the risk of a photosensitive seizure, as may dimming the brightness of video content and dimming the brightness of an external environment, for example using per pixel polarisers.

In some examples, the augmented reality data 22 comprises audio content, and the at least one characteristic of the augmented reality data is any of audio volume, audio frequency, presence of audio, or number of audio sources provided as audio content. Reducing audio volume and/or number of audio sources may reduce a number of stimuli present in the augmented reality data 22, which may be beneficial for ADHD behavior and for users suffering with autism, for example.

In some examples, the augmented reality data 22 comprises light provided to the user 24 of the device 10, and the at least one characteristic of the augmented reality data is any of light intensity, light colour, presence of light, or light flash rate. Modifying the properties of light provided to the user 24 may, for example, mitigate for upcoming travel to a different time zone by acclimatizing the user 24 to the light experienced in the destination time zone prior to travel. Blue light may be useful for mitigating the effects of jet lag. Increased light intensity and/or brighter light colours may find utility in mitigating the effects of depression and/or SAD, for example.

In some examples, the augmented reality data 22 comprises a visual object provided to a user of the device, and the at least one characteristic of the augmented reality data is any of a boundary of the visual object, an indicator of the visual object, a transparency of the visual object, an image type of the visual object, a size of the visual object, a colour of the visual object, and a presence of the visual object. This visual objects may be modified in a number of ways to mitigate for potential changes to a health condition of the user 24 of the device 10.

Modifying the augmented reality data 22 may involve increasing a transparency of a virtual object forming part of the augmented reality data 22. For example, the virtual object may be made more transparent in the scene so as to reduce the impact of the virtual object to the user 24 of the device 10. Modifying the augmented reality data 22 may involve converting a visual representation of a virtual object to a wire-frame model. For example, the virtual object may include surface characteristics such as texture in the augmented reality data. The virtual object may be converted to a wire-frame model by specifying the edges of the virtual object or connecting constituent vertices of the virtual image object using straight lines or curves. The surface characteristics of the virtual object may be removed, or at least not displayed, when converting the virtual image object to the wire-frame model. Converting the visual representation of the virtual object to a wire-frame model may allow visualization of the underlying recognized object without the full stimuli associated with the object, thereby reducing the impact of the object on the user 24 of the device 10.

In some examples, the augmented reality data comprises data indicative of external environment conditions perceived by a user of the device, and the trigger comprises a change to the perceived external environment conditions. For example, the augmented reality data may comprise an augmented or virtual representation of the external environment of the user 24 of the device 10, and the augmented reality data may be modified to mitigate for a change to the external environment. A change in weather is one such example of a change in environment which may be mitigated for by the device 10, as a change in weather may negatively impact a mood of the user 24 of the device 10. In some examples, the data indicative of external environment conditions may comprise objects present in the perceived external environment conditions. A modification may be made to the augmented reality data 22 to reduce the impact of and/or remove an object present in the perceived external environment conditions.

In some examples, the augmented reality data 22 retains data indicative of potential hazards to a user of the device in spite of any modification to the augmented reality data 22. This may allow for appropriate modification of the augmented reality data 22 whilst minimizing the risk of negative impact to the user 24.

In some examples, the receiver 12 is operable to receive historic data indicative of a historic health condition of a user 24 of the device 10. This may provide for increased accuracy in detection of the trigger as the user's pre-existing health conditions may be known. The historic data may comprise captured data of the current user of the device 10, and/or may comprise captured data of at least one previous user of the device 10. In such a manner, a database of health conditions may be used, which may allow for more accurate identification of the trigger.

In some examples, the receiver is operable to receive real-time data indicative of a health condition of a user of the device. This may allow the device 10 to react to modify the augmented reality data 22 in real time. The receiver may be operable to receive both historic data and real-time captured data indicative of a health condition of a user of the device, the processor may configured to compare the historic data and the real-time data, and responsive to the comparison the processor may be configured to identify a trigger indicative of a change in the health condition of a user.

In some examples, the processor 14 may be configured to process the captured data to identify first and second triggers indicative of a possible change in the health condition of a user. The content processing state of the content processing component 16 may be modified such that first and second characteristics of the augmented reality data 22 are modified. The first characteristic may comprise a visual object of the augmented reality data 22, and the second characteristic may comprise an audio object of the augmented reality data 22. In such an example, the content processing component 16 may comprise first and second content processing components and the content transducer 18 may comprise first and second content transducers.

In some examples, the processor 14 may be configured to process the captured data to identify a first trigger indicative of a possible change in a first health condition of a user 24 and a second trigger indicative of a possible change in a second health condition of the user 24, in response to the first trigger modify the content processing state of the content processing component 16 such that a first characteristic of the augmented reality data 22 is modified, and in response to the second trigger modify the content processing state of the content processing component 16 such that a second characteristic of the augmented reality data 22 is modified. In such an example, the receiver 12 may be operable to receive captured data indicative of the first and second health conditions of the user 24. The first characteristic may comprise a visual object of the augmented reality data 22, and the second characteristic may comprise an audio object of the augmented reality data 22. In such an example, the content processing component 16 may comprise first and second content processing components and the content transducer 18 may comprise first and second content transducers.

It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the accompanying claims.

What is claimed is:

1. A device comprising:
   a content processing component operable in a content processing state;
   a content transducer configured to provide augmented reality data to a user of the device based on an output of the content processing component, wherein providing augmented reality data to the user of the device involves presenting one or more virtual objects to the user;
   a receiver operable to receive captured data indicative of a health condition of a user of the device; and
   a processor configured to;

process the captured data to identify a trigger indicative of a possible change in the health condition of a user; and
   in response to the trigger, modify the content processing state of the content processing component such that at least one characteristic of the augmented reality data is modified; and
   wherein the receiver comprises a software application for receiving schedule information of a user of the device, and the trigger comprises a determination from the schedule information that the user intends to travel to another time zone,
   wherein the modification of the at least one characteristic of the augmented reality data includes obscuring or removing at least one of the one or more virtual objects.

2. A device as claimed in claim 1, wherein the receiver comprises an eye tracking sensor for monitoring location of an eye of a user of the device and the trigger comprises eye movements of a user of the device.

3. A device as claimed in claim 1, wherein the trigger comprises fixation of an eye of a user on at least one attribute of the augmented reality data.

4. A device as claimed in claim 1, wherein the receiver comprises an eye tracking sensor for monitoring a size of a pupil of a user of the device, and the trigger comprises dilation of a pupil of a user of the device.

5. A device as claimed in claim 1, wherein the receiver comprises an electrical potential sensor for monitoring electrical potential signals of a user of the device, and the trigger comprises a pattern in monitored electrical potential signals.

6. A device as claimed in claim 1, wherein the receiver comprises a microphone, and the trigger comprises an increase in noise levels and/or number of audio sources received by the microphone in use.

7. A device as claimed in claim 1, wherein the receiver is operable to receive user monitoring captured data and environmental sensor monitoring data, and the processor is configured to process the user monitoring captured data and the environmental sensor monitoring data to identify the trigger indicative of a possible change in the health condition of a user.

8. A device as claimed in claim 1, wherein the receiver comprises an object recognition system for recognising objects of an external environment of a user of the device, and the trigger comprises an object of an external environment of a user of the device.

9. A device as claimed in claim 1, wherein the receiver comprises a motion tracker for tracking motion of a head of a user of the device, and the trigger comprises a determination of a position of a head of a user of the device.

10. A device as claimed in claim 1, wherein the augmented reality data comprises at least one of a visual object and an audio object.

11. A device as claimed in claim 1, wherein the augmented reality data comprises video content, and the at least one characteristic of the augmented reality data is any of video content brightness, video content speed, video content quality, number of objects provided as video content, presence of video content, or refresh rate of video content.

12. A device as claimed in claim 1, wherein the augmented reality data comprises audio content, and the at least one characteristic of the augmented reality data is any of audio volume, audio frequency, presence of audio, or number of audio sources provided as audio content.

13. A device as claimed in claim 1, wherein the augmented reality data comprises light provided to a user of the device, and the at least one characteristic of the augmented reality data is any of light intensity, light colour, presence of light, or light flash rate.

14. A device as claimed in claim 1, wherein the augmented reality data comprises a visual object provided to a user of the device, and the at least one characteristic of the augmented reality data is any of a boundary of the visual object, an indicator of the visual object, a transparency of the visual object, an image type of the visual object, a size of the visual object, a colour of the visual object, and a presence of the visual object.

15. A device as claimed in claim 1, wherein the augmented reality data comprises data indicative of external environment conditions perceived by a user of the device, and the trigger comprises a change to the perceived external environment conditions.

16. A device as claimed in claim 1, wherein the augmented reality data retains data indicative of potential hazards to a user of the device in spite of any modification to the augmented reality data.

17. A device as claimed in claim 1, wherein the receiver is operable to receive data indicative of any of attention deficit hyperactivity disorder, epilepsy, autism, depression, seasonal affective disorder, or jetlag.

18. A device as claimed in claim 1, wherein the device comprises or is comprised in a headset.

19. A device as claimed in claim 1, wherein the receiver is operable to receive historic data indicative of a historic health condition of a user of the device.

20. A device as claimed in claim 1, wherein the receiver is operable to receive real-time data indicative of a health condition of a user of the device.

21. A device as claimed in claim 1, wherein the receiver is operable to receive both historic data and real-time data indicative of a health condition of a user of the device, the processor is configured to compare the historic data and the real-time data, and responsive to the comparison the processor is configured to identify a trigger indicative of a change in the health condition of a user.

* * * * *